(12) United States Patent
Zoorob

(10) Patent No.: US 8,226,987 B2
(45) Date of Patent: Jul. 24, 2012

(54) HERBAL PREPARATION TO RELIEVE INFLAMMATION AND SMOOTH MUSCLE CONTRACTION

(76) Inventor: George K. Zoorob, Colorado Springs, CO (US)

( * ) Notice: Subject to any disclaimer, the term of this patent is extended or adjusted under 35 U.S.C. 154(b) by 55 days.

(21) Appl. No.: 11/062,715

(22) Filed: Feb. 22, 2005

(65) Prior Publication Data

US 2006/0188588 A1 Aug. 24, 2006

(51) Int. Cl.
*A61K 36/537* (2006.01)
*A61K 36/53* (2006.01)
*A61K 36/23* (2006.01)

(52) U.S. Cl. .......... 424/725; 424/746; 424/745; 514/899

(58) Field of Classification Search .................. None
See application file for complete search history.

(56) References Cited

U.S. PATENT DOCUMENTS

| 6,322,823 B1 * | 11/2001 | Mannella |
| 2001/0024664 A1 | 9/2001 | Obukowicz et al. |
| 2004/0224020 A1 * | 11/2004 | Schoenhard |

FOREIGN PATENT DOCUMENTS

| EP | 1178104 A1 * | 2/2002 |
| JP | 08268851 A * | 10/1996 |

OTHER PUBLICATIONS

Ostad, S. N. et al. Journal of Ethnopharmacolgy (2001), 76: 299-304. The effect of fennel essential oil on uterine contraction as a model for dysmenorrhea, pharmacology and toxicology study.*
Bouzouita, N. et al. Flavour & Fragrance Journal (2003); 18(5): 380-383. Antimicrobial activity of essential oils from Tunisian aromatic plantns.*
Wormwood, V. A. The Complete Book of Essential Oils and Aromatherapy. McMillan London Limited, 1991, USA. pp. 227-233.*
Lawless, J. The Illustrated Encyclopedia of Essential Oils: The Complete Guide to the Use of Oils in Aromatherapy and Herbalism. Element Books, 1995, USA. pp. 109, 129, 211-213 and 227.*
Lawless, J. The Illustrated Encyclopedia of Essential Oils: The Complete Guide to the Use of Oils in Aromatherapy and Herbalism. Element Books, 1995, USA. pp. 109, 129,211-213 and 227.*
Sivropoulou A et al. J. Agric. Food Chem. (1997); 45(8): 3197-3201. Antimicrobial, cytotoxic and antiviral activities of *Salvia fructicosa*.*
Goren, A C et al. Verlag der Zeitschrift fur Naturforschung (2003); 53c: 687-690. Analysis of essential oil of *Cordiothymus capitatus* (L.) and its antibacterial and antifungal activity.*
Bouzouita, N et al. Flavour & Fragrance Journal (2003); 18(5): 380-383. Antimicrobial activity of essential oils from Tunisian aromatic plants.*

Shetty, R S et al. World Journal of Microbiology & Biotechnology (1994); 10: 232-233. Antimicrobial properties of cumin.*
Sayyah, M. et al. Iranian Biochemical Journal, Oct. 2002; 6(4): 141-145. Anti-nociceptive effect of the fruit essential oil of *Cuminum cyminum* L. in rat.*
Wagner, H. et al. Planta Medica, 1986; 6: 549. Screening of essential oils and phenolic compounds for in-viro inhibition of prostaglandin biosynthesis.*
Baricevic, D et al. Medicinal and Aromatic Plants—Industrial Profiles (2000), 14(Sage), 143-184.*
Leonard Bielory, Complementary & altrenative inventions ifn asthma and immunology, Ann.Allergy Asth.Immun. 2004:93 (Suppl) S45-S54.
Michael Boxer, et al. Cumin Anaphylaxis, J. Allergy COn. Immun. 1997:99:722-3.
Pierre R. Burkhard, et al. Plant-induced seizures, J. Neuro. (1999): 667-670.
Andrew S. Coco, Primary dysmenorrhea, American Family Physician, (1999) vol. 60: 489-496.
R. Eccles, Methol and Related Cooling Compounds, J. Pharm Pharmacol. 1994, 46:618-630.
M. Brian Fennerty, Traditional therapies for Irritable Bowel Syndrome, Reviews in Gastroent. disorders, (2003) 3: S 2 : 518-524.
Hali Gali-Muhtasib, Traditional uses of *Salvia libanotica*, Ethnopharmacol. (2000) 71:513-520.
Marcin Golec, et al. Immunological reactivity to . . . dust from herbs, Ann. Agri. Environ. Med. (2004) 11: 121-127.
Maria Gomes-Carneiro et. al. Mutagenicity Testing . . . Mutation Res. (1998) 416: 129-135.
T.Ishidah, et al. Terpennoid biotransformation, Xenobiotica (1989)19:843-855.
Jaeger Jailwala, et al. Pharmacological Treatment of Irritable Bowel Syndrome, Ann. Internal Med. (2000) 133:136-147.
Paul J. Kassebaum, et al. Possible warfarin interaction with menthol, The Annals of Pharmacoltherapy, (2005) 39:365-367.
Claudia Kohlert, et al. Thymol in humans, J. Clin. Pharmacol. (2002) 42: 731-737.
Alan C. Logan, et al. Treatment of small intestinal bacterial overgrowth with peppermint. Altrnative Medicine Review (2002)7:410-417.
A. Madisch, et al. Treament of functional dyspepsia with a herbal preparation, Digestion, (2004) 69:45-62.
H. Schilcher, Effects and side-effects of essential oils, Essential Oils and Aromatic Plants, ISBN 90-247-3195-X !985, Dordrecht, NL.
W. J. Waddell, Threshold of Carcinogenicity of Flavors, Toxicol. Sci. (2002) 68: 275-2799.
Bek'Tal Tepe, et al. Essential oils and extracts of *Thymus eigil*, Food Chem. (2004) 52:1132-1137.
N. Szentandrassy, et al. Effect of thymol, BMC Pharmacology (2003) 3: 9.

* cited by examiner

*Primary Examiner* — Michele Flood
(74) *Attorney, Agent, or Firm* — Lathrop & Gage LLP

(57) ABSTRACT

An herbal preparation comprised of sage, thyme and cumin is found to relieve the symptoms of inflammation and smooth muscle contraction. The preparation preferably comprises sage, thyme and cumin in the proportions 0.50, 0.43 and 0.07 respectively. The symptoms of menstrual cramps and asthma are relieved by administration of the preparation.

6 Claims, No Drawings

HERBAL PREPARATION TO RELIEVE INFLAMMATION AND SMOOTH MUSCLE CONTRACTION

FIELD OF THE INVENTION

This invention relates to herbal preparations to relieve inflammation and smooth muscle contraction, in particular for the relief of prostaglandin and TNF-α mediated conditions.

BACKGROUND OF THE INVENTION

Several medical conditions involve smooth muscle contraction and inflammation due to the effects of prostaglandins and other hormones produced within the body. Symptomatic relief has been achieved with naturally-occurring or synthetic small molecules. There has been little information about the use of herbal remedies for symptomatic relief.

The enzyme cyclooxygenase is rapidly induced upon exposure to agents such as hormones, cytokines and growth factors with the resulting formation of prostaglandins. COX starts a cascade of reactions which convert the fatty acid arachidonic acid to one of a group of prostaglandin molecules, a group of hormones that cause a number of effects such as maintaining smooth muscle tone, controlling the production of stomach acid and participation in inflammation and blood clotting. It is thought that prostaglandins are also direct pain signals. Among the many conditions that result from the action of prostaglandins are menstrual cramps, asthma, pain and inflammation. There are two varieties of cyclooxygenases, which are present in various tissues. COX-1 is considered to be important in controlling the production of stomach acid and the aggregation of platelets. Inhibition of COX-1 results in the increased production of stomach acid and reduces platelet aggregation; these combined effects may lead to stomach and duodenal ulcers and bleeding. COX-2 is considered to be important in controlling smooth muscle contraction, pain and inflammation. Inhibition of COX-2 results in reduction of cramping, pain and inflammation.

Dysmennorrhea is an exemplar condition. As many as 40 million women in the United States alone suffer from menstrual cramps with associated bloating, backache, fatigue, mood swings, excessive bleeding and nausea. These symptoms are caused by the hormonal fluctuations accompanying menstruation, when prostaglandins are produced in the uterine lining, causing uterine smooth muscle contractions, reducing blood flow and temporarily cutting off oxygen supply to the tissues. These contractions are felt as menstrual cramps. While most woman experience at least some cramping, in others higher than normal levels of prostaglandins cause severe menstrual cramps that are incapacitating. Whether mild or severe, women suffering from menstrual cramps seek relief.

Arthritis is a well-known inflammatory condition. Inflammation of the joints results in severe pain, deformation and inanition. Arthritis occurs either as a result of an immune-type inflammation (rheumatoid arthritis) or can result from wear and tear on the joints (osteoarthritis). The condition often progresses to the point where artificial joints are used to replace the arthritic joints.

Tumor Necrosis Factor-α (TNF-α) is a proinflammatory, multifunctional cytokine which is released by mast cells and macrophages in response to environmental triggers, and has been implicated in the pathophysiology of inflammatory diseases. Anti-TNF-α therapy has been approved to treat Crohn's disease and rheumatoid arthritis. A prevalent condition that is mediated by prostaglandins and TNF-α is asthma. The incidence of asthma is increasing worldwide. It is characterized by wheezing and shortness of breath, leading in some cases to respiratory failure and death. The production of prostaglandin in response to viral or bacterial infection, exercise, allergic or environmental stimuli such as cold or dehydration leads to contraction of the smooth muscles of the bronchi, causing obstruction of the airways. TNF-α release causes inflammation with bronchiolar edema and mucus production, which exacerbates the condition. Treatment for asthma is twofold: "rescue" drugs such as epinephrine (injected or inhaled) or albuterol are administered during an acute attack and are followed by maintenance therapy to reduce or eliminate the bronchospasm reaction. The most common maintenance therapy includes the avoidance of triggering factors such as animal or food allergies and anti-inflammatory drugs such as steroids. In recent years, additional maintenance drugs have been marketed which intervene at other points in an asthmatic attack.

There are many drugs available to treat inflammatory conditions. Aspirin, a drug used for more than 150 years, was the first synthetic drug used to treat pain. When it was discovered that aspirin acted by inhibiting prostaglandin synthesis, pharmaceutical manufacturers devised many other synthetic drugs that acted in the same manner, commonly termed NSAIDs (non-steroidal anti-inflammatory drugs). Among these are ibuprofen, naproxin and the so-called COX-2 inhibitors. The goal has been to inhibit COX-2 while minimizing COX-1 inhibition. While these drugs, like aspirin, are effective, they may cause side effects. Manufacturers of pain relievers spend millions of dollars in advertising to convince the public that these drugs are a safe and effective way to deal with headache, arthritis and menstrual cramps. In fact, however, more than 100,000 Americans were hospitalized each year from taking over-the-counter pain relievers, with about 20,000 deaths. The most common side effect is gastrointestinal distress with discomfort and bleeding, which can be severe. Less common side effects include drowsiness, confusion, kidney damage and liver damage.

Many persons prefer a natural, non-synthetic drug preparation to a synthetic drug. Herbal preparations offer an alternative to synthetic drugs. Dr. Duke's Phytochemical and Ethnobotanical Database (www.ars.grin.gov/duke) lists botanicals and references publications claiming activities which range from anti-inflammatory uses to anti-cancer treatments. Particularly, plants in the Lamiaceae "mint" family have been used for both their culinary and healthful properties. The mint family includes about 200 genera, such as Salvia (sage), Rosmarinus (rosemary), Mentha (mint), Ocimum (basil), Thymus (thyme), Marrubium (hoarhound), and Nepeta (catnip). Another family with useful properties is the Apiaceae (cumin) group.

The need remains to identify herbal preparations which will give relief from inflammatory conditions and smooth muscle contractions.

SUMMARY OF THE INVENTION

This invention provides herbal preparations for the relief of inflammation and smooth muscle contraction. The first preparation is a combination of thyme, sage and cumin. Preferably, the leaves of thyme and sage and cumin seeds are used. The thyme, sage and cumin may be obtained from plants grown in any climate, but preferably these plants are grown in a Mediterranean climate, that is, a warm, sunny, dry climate. The preferred species of thyme is *Thymus captitatus*. The preferred species of sage has high levels of camphor and eucalyptol and low levels of the toxin thujone. The most preferred species is *Salvia fruticosa* or *S. triloba*. The preferred species of cumin is *Cuminum cyminum*.

The herbal preparations may be leaves and seeds, but more conveniently, the active agents are extracts. The agents (also termed "essential oils") may be extracted by distillation, oil extraction or other known methods of isolation. They are also widely available commercially.

The herbal preparations are administered as a tisane, as a liquid or, most preferably, in a soft gel capsule. The herbs or extracts are mixed in the following proportions:

TABLE I

| Ingredient | Effective range | Most preferred proportion |
|---|---|---|
| Sage | 0.30 to 0.60 | 0.50 |
| Thyme | 0.30 to 0.60 | 0.43 |
| Cumin | 0.05 to 0.10 | 0.07 |

When administered as a tisane, one to five grams total of herbs are steeped in hot water and the tisane is ingested as needed. Sugar or other flavorings may be added.

When administered in liquid form, the herbs or extracts are ingested neat or may be mixed in any convenient solvent such as water, fruit juice. The mixture is taken as needed. The preferred dosage is equivalent to 50 to 200 mg total of essential oils, most preferably about 140 mg. The mixture should not be taken more than four times in any 24-hour period. Flavoring such as peppermint may be added.

Gel capsules of the herbal preparations are prepared. Most conveniently, essential oil extracts are mixed in the above proportions and inserted into soft gelatine capsules. The amount of essential oils totals 30 to 100, most preferably 70 mg per capsule. For convenience in handling, the essential oils are mixed with carrier oils, which may be medium-chain fatty acids and olive oil. Lecithin may be added. For the relief of menstrual cramps, two capsules are administered at the onset of symptoms.

DETAILED DESCRIPTION OF THE INVENTION

An outstanding characteristic of the useful herbs noted above is their pungent odor, which is due to the high content of volatile aromatic and essential oils contained in the leaves and seeds. Many of these herbs have been used for millennia for flavorings and for medicinal purposes. Various species within each genus vary in the content and composition of the active components. the composition is strongly affected by climate. It has been found by Applicant that herbs grown in a Mediterranean climate have the highest content of active agents and low content of toxins. Combinations of one or more of these herbs have been found to have a heightened beneficial effect. Applicant has combined thyme, sage and cumin to produce a preparation that is quick acting and efficacious in easing the symptoms of Dysmennorrhea, a COX-2 mediated condition caused by uterine contractions triggered by prostaglandin synthesis initiated by the hormonal changes accompanying menstruation. It is believed that the beneficial effect of the preparation is due to direct inhibition of COX-2 in the uterine lining. However, Applicant is not bound by theory and by COX-2-mediated condition is meant any condition that is controlled by products of the prostaglandin cascade of reaction, whether the inhibition is at the COX-2 reaction or at enzyme reactions further in the cascade. Applicant has found that thyme *Thymus capitatus*, is especially useful for inhibiting prostaglandin synthesis. Thyme grown in Mediterranean climates is especially high in the active agents thymol and carvacrol. Sage is a common plant that grows wild or cultivated across the earth. Common sage contains high levels of thujone, a toxin. Greek sage or *Salvia fruticosa* (also known as *S. triloba*.) has the least amount of thujone and the highest amount of the active agents camphor and eucalyptol. The beneficial effects of thyme are heightened when combined with sage. Effects are further heightened by combination with *Cuminum cyminum*. Any cumin will be acceptable except that the area and climatic conditions affect the content of essential oils. The Mediterranean species are especially high in these agents.

Active agents are present in all parts of the plants. Most conveniently, thyme and sage leaves and cumin seeds are used. A tisane of active agents may be prepared by steeping the ground leaves and seeds with hot water. The active agents may be more conveniently and compactly administered by combining oil extracts of the thymus, sage and cumin. Such extracts are commercially available. The most convenient method of administration is via a soft gel capsule.

Not being bound in scope to the following embodiments, Applicant now describes how to make and use preferred embodiments of the invention.

Example 1

Gelcaps

Herbal extracts of essential oils are combined in the following proportions:

TABLE II

| Essential oil extract of: | Composition Range w/v | Preferred amount |
|---|---|---|
| Thyme | 40-50% | 43% |
| Sage | 30-60% | 50% |
| Cumin | 5-20% | 7% |

The essential oils are combined with medium-chain triglycerides and extra-virgin olive oil as diluent and carrier. The combination is inserted into soft gelatin-glycerol capsules.

Example 2

Use of the Gelcaps to Treat Menstrual Cramps

Gelcaps containing a total of 70 mg total essential oils are taken at the first sign of menstrual cramps. The recommended dosage is two gelcaps every four to six hours as needed. It is recommended that no more than eight gelcaps should be taken in each 24 hour period. Relief is observed in 17-20 minutes This gelcap will dissolve in 5-7 minutes and absorption is rapid.

It has been found that within minutes, the uterine muscle is relaxed and the symptoms of cramps, bloating, nausea, backache, headache, fatigue and mood swings are relieved. Relief lasts for hours.

A trial was established to test the above dosage and regimen. Forty healthy women who reported menstrual cramps were given gelcaps containing 70 mg of the essential oil combination of Table II. They were asked to complete a questionnaire detailing the frequency and severity of cramps, the time of relief following ingestion of the gelcaps and the time elapsed before cramps returned. One patient reporting very severe cramping but no relief after ingesting the gelcaps was not included in the following Table III.

TABLE III

| AGE | | SEVERITY 1 = mild 10 = severe | | MINUTES TO RELIEF | | HOURS TO RECURRENCE | |
|---|---|---|---|---|---|---|---|
| range | average | range | average | range | average | range | average |
| 13-48 | 32.4 | 4-10 | 7.2 | 2-120 | 21 | 4-24 (n = 24) no recurrence (n = 15) | 9.4 |

It should be pointed out that most of the subjects reporting no recurrence of cramping had taken a second and in some cases a third dose of gelcaps every four hours. No side effects were reported except for an aftertaste of herbs.

A continuation of the trial confirmed the above results. 68 women were enrolled; 55 were interviewed and completed a questionnaire. After taking two gelcaps containing the essential oils of Table II, patients reported 95% treatment efficacy, with 56% finding relief for more than 24 hours; 42% had no recurrent cramps after 3 days. 23% had relief for six hours or less, while 5% had no significant relief. The onset of relief was rapid. 47% of the patients were relieved within 20 minutes, 76% within 30 minutes and 95% within 60 minutes.

Seventeen of the respondents were randomly selected and underwent urinalysis to evaluate prostaglandin levels prior to taking the gelcaps and a follow up urinalysis three hours later. It was found that $PGF_{2\alpha}$ showed a fairly consistent decline after the first dose of gelcaps. However, the PGE2 levels did not show as consistent a decline or no change. Pharmacologically, the effect of $PGF_{2\alpha}$ on uterine muscle is well known to be a more potent modulation of smooth muscle contraction than is that of PGE2.

Example 3

Liquid Preparations

"Tea" bags were made with ground herbs. For this use, 1.5 grams total of sage, thyme and cumin in the proportions 55%, 35% and 10% were inserted into a porous cheesecloth bag. The bag was steeped in one cup of hot water and resulting tisane ingested by women suffering from menstrual cramps. The tisane is especially useful when taken at bedtime. The relaxing effects allow for a good night's sleep.

The extracts can be administered directly, that is, not in a gelcap or tisane. A mixture of essential oils as for Example 1 may be taken directly by spoon. Relief was even more rapid than with the gelcaps, being observed in as little as five minutes. The recommended unit dosage is two teaspoonfuls, or about 10 ml, which gives the desired dosage of about 140 ml. As for the gel capsules, it is recommended that dosages should not exceed four times in a 24-hour period.

Example 4

Acute Oral Toxicity of the Essential Oil Blend

An acute oral toxicity study was carried out in the rat to assess the toxic characteristics of the composition of Example 1, when administered orally to rat by gavage in a single dose. The objective of this study was to determine health hazards, if any, that could arise from acute overdosage in humans. Data served as a basis for establishing a dosage regimen for sub- chronic studies and provided initial information on the mode of toxic action of the composition.

The study was conducted in compliance with the OECD Guidelines for Testing of Chemicals (No. 420, Section 4: Health Effects) on conduct of "Acute Oral Toxicity—Fixed Dose Method" (adopted Dec. 17, 2001).

The protocol was as follows:

Test system: Rat, strain Sprague Dawley

Age: 9 to 20 weeks

Body Weight Range: 171.2 to 198.3 grams at initiation

Identification: By cage tag and corresponding color body marking

No. of close groups: I: Sighting study, one female, dose 5000 mg/kg II: Main study, four females, five males, dose 5000 mg/kg Acclimatization: One week in experimental room after veterinary examination. The room was air conditioned with 10-15 air changes per hours, temperature was held between 19-25° C., relative humidity 50-60%, artificial fluorescent illumination cycle set at 12 hours light, 12 hours dark.

Randomization: After acclimatization and veterinary examination, animals were randomly selected.

Nutritional Condition: Fasted overnight prior to treatment. Food was offered three hours after dosing.

Accommodation: Single or group housed in polypropylene cages with stainless steel grid top, facilities for food and water bottle, and bedding of clean paddy husk.

Diet: "Amrut" brand pelleted rat feed provided ad libitum.

Water: Well water passed through activated charcoal filter and exposed to UV ray was provided ad libitum in glass bottles with stainless steel sipper tubes.

In a sighting study, one female rat was administered the composition of Example 1 at a dose of 5000 mg/kg body weight. The rat was observed for mortality and clinical signs for 14 days post-dosing. No mortality or signs of evident toxicity were encountered. In the main study, the undiluted composition was orally administered as a single dose to a group of four female and five male rats at the dose of 5000 mg/kg body weight. Food was withheld overnight prior to the administration of the test article, however, water was available ad libitum during this period. The rats were then observed for incidence of mortality and signs of intoxication for 14 days.

The test article was administered by oral gavage to each rat as a single does, using a suitably graduated syringe and a stainless steel 16G intubation needle. The dose administered to individual rats was adjusted according to its body weight recorded just prior to dosing. Food was offered four hours after dosing.

The composition did not cause any mortality in rats treated at 5000 mg/kg following dosing and during the observation period of 14 days post-dosing. No abnormal clinical signs were observed in treated rats throughout the observation period. No adverse effects on body weight were seen, not were gross pathological alterations in body organs detected on terminal necropsy.

Example 4

In Vitro Inhibition of Uterine Contraction

Primary Dysmennorrhea is the direct result of high levels of prostaglandins. The oil composition of Table II was evaluated for its inhibitory activity in uterine contractions induced by prostaglandins PGF2α and PGE2 in isolated rat uterus preparation.

A study was carried out to determine the effect of the composition of Table II on the rat isolated virgin non-pregnant uterus smooth muscle. The uterine contraction was induced by prostaglandins (PGF2α and PGE2). The effect on uterine contractility induced by prostaglandins was evaluated at 25, 50 and 100 μg/ml of the test substance. One gram (1.08 ml) of the test substance was suspended in 10 ml 90% ethanol and sonicated for 15 minutes. The resulting suspension of 100 mg/ml thus prepared was whitish in color. One ml of the suspension was diluted with De Jalon solution (154 mM NaCl; 5.6 mM KCl; 0.55 mM $CaCl_2$, 6.0 mM $NaHCO_3$; 2.78 mM Glucose) to obtain a final concentration of 100 μg/ml; 50 μg/ml and 25 μg/ml. The uterine contractile agents PGF2α and PGE2 were likewise dissolved in De Jalon solution. Further dilutions were also made in De Jalon solution.

The protocol was:
Test system: Rat, virgin female, strain Wistar
Age: 6 to 8 weeks
Weight: 180-200 grams.
Acclimatization: One week in experimental room. The room was air conditioned with 10-15 air changes per hours, temperature was held at 22+/-° C., relative humidity 40-70%, artificial fluorescent illumination cycle set at 12 hours light, 12 hours dark. Bedding was sterilized husk
Randomization: Two days prior to study, animals were randomly selected.
Accommodation: Four rats per cage
Diet: "Purina Certified Rodent Chow" brand pelleted rat feed provided ad libitum.
Water: Filtered, deionized water was provided ad libitum in glass bottles with stainless steel sipper tubes.

The virgin female rats were administered stilboesterol (1 ml/kg of 0.1 mg/ml.) intraperitoneally for two days. On the third day, vaginal smears were taken and examined for evidence of estrus. Only those animals showing frank estrus were chosen for the study. On the day of the experiment, the vaginal smear was obtained for each animal to observe the sexual cycle of the animal. Upon confirmation of estrus, the rats were euthanized with pentobarbitol (100 mg/kg, i.p.). The abdomen was cut open and the uterine horns were identified, removed. and placed in De Jalon solution. The adhering tissue from the uterine horns was gently excised and the horns were cut into strips of 15 mm size and mounted in a tissue bath containing 30 ml of De Jalon solution. The organ bath was maintained at 31-32° C. and aerated continuously. One end of the tissue was tied to the glass holder and the other end was tied to the frontal writing lever of a smoked kymograph drum under a resting tension of 0.5 g.

Before the start of the experiment, trial was performed to observe the effect of the solvent used for the preparation of the test substance. The DRC of PGF2α was obtained in De Jalon solution and in De Jalon solution containing 0.1 ml of 90% ethanol in 11 ml of De Jalon solution. For PGE2 induced contraction, the procedure was the same except that the starting concentration of PGE2 was 20 μg/ml.

After an equilibration period of 30-40 minutes, the graded dose response curve (DRC) of PGF2α at a starting concentration of 1 μg/ml was recorded on the kymograph. After obtaining the DRC the tissue was incubated for 15 minutes with the De Jalon solution containing 25 mg/ml of the test solution. The De Jalon solution was drained and fresh De Jalon solution was used to incubate the tissue for 15 minutes with every five minute wash. Afterwards the DRC of PGF2α was taken again. If the RC matched the DRC before the incubation of the test substance, then the experimented was continued. The next incubation was with De Jalon solution containing 50 μg/ml of test agent and the washout and retested were repeated. A similar procedure was performed with 100 μg/ml of the test substance. The experiment was repeated on an additional two uterine preparations. Later the DRC of PGE2 was determined and similar experiments were performed with PGE2.

The DRC of PGF2α and PGE2 in the absence and presence of 25, 50 and 100 μg/ml of test substance was converted into log DRC and the EC50 (effective concentration of the test substance to produce 50% contractile response) of PGF2α and PGE2 was evaluated. The Dose ratio was calculated by the formula:

$$\frac{EC_{50} \text{ in presence of the test solution}}{EC_{50} \text{ in absence of the test solution}}$$

The percentage of inhibition was calculated by the formula:

$$\frac{100 - \text{Magnitude of the response after exposure to the test solution}}{\text{Magnitude of the response before exposure to the test solution}} \times 100$$

The data were subjected to non-parametric method of analysis using Krushal-Wallis test followed by Dunn's multiple comparison test.

The results from three separate experiments for each point are summarized in Table IV.

TABLE IV

| μg/ml Test Solution | $EC_{50}$ value of PGF2α (μg) | Dose ratio | % inhibition | $EC_{50}$ value of PGE2 (μg) | Dose ratio | % inhibition |
|---|---|---|---|---|---|---|
| 0 | 1.1 ± 0.04 | — | — | 1.8 ± 0.09 | — | — |
| 25 | 2.0 ± 0.12 | 1.8 ± 0.09 | 25.7 ± 2.9 | 2.5 ± 0.14 | 1.4 ± 0.14 | 4.5 ± 1.21 |
| 50 | 3.8 ± 0.12 | 3.5 ± 0.23 | 63.0 ± 1.0 | 4.1 ± 0.15 | 2.3 ± 0.16 | 3.3 ± 1.3 |
| 100 | 7.1 ± 0.49 | 6.5 ± 0.62 | 77.4 ± 1.8 | 5.7 ± 0.35 | 3.2 ± 0.06 | 29.7 ± 5.3 |

In the rat uterus preparation, all concentrations of test solution incubated during the 15 minute test caused concentration dependent rightward displacement of DRC of PGF2α and PGE2. Though there was an increase in EC50 values of both prostaglandins in the presence of increasing concentrations of test solution, only test solution at 100 μg/ml was able to significantly increase (p<0.05) the EC50 value from 1.1+/−0.04 to 7.1+/−μg for PGF2α and 1.8+/−0.09 to 5.7+/−0.35 μg for PGE2. In a dose dependant manner, there was prominent increase in dose ratio for both prostaglandins.

In conclusion, the test solution has certain ingredients to inhibit the contractions induced by PGF2α and PGE2 by virtue of non-competitive antagonism. The test substance has more specific inhibitory activity on PGF2α than compared to $PGE_2$.

Example 4

Preliminary Experiment to Assay Anti-TNF-α Activity

A preliminary in vitro experiment using isolated leukocytes shows that the composition of Example 1 shows a highly significant TNF-α inhibitory activity. Based on these preliminary results, further in vitro and in vivo experiments are expected to show utility in the treatment of inflammatory conditions such as asthma.

A. Guinea pigs or rats will be sensitized with egg albumin and after a specific period, will be challenged with insufflated or injected egg albumin or histamine. The protective effect of the composition of Example 2 will be assayed.

B. An indirect acute asthmatic attack model will be performed by introducing a spasmogen such as histamine, LTD4 and methacholine vis tracheal cannulation into the guinea pig lung. The bronchoconstriction will be relieved with the composition of Example 1. Bronchial alveolar lavage will be performed to follow the inflammatory cell infiltration.

The invention claimed is:

1. A preparation of essential oils in an effective amount for relieving symptoms of inflammation and smooth muscle contraction in a human comprising sage (*Salvia triloba*) 30% to 60% weight to volume of the preparation, thyme (*Thymus capitatus*) 30% to 60% weight to total volume of the preparation and cumin (*Cuminum cyminum*) 5% to 20% weight to total volume of the preparation.

2. The preparation of claim 1 wherein sage, thyme and cumin are combined in the proportions 50%, 43%, and 7% weight to total volume of the preparation respectively.

3. A method of relieving symptoms of inflammation and smooth muscle contraction in a human (*Homo sapiens*) comprising: administering an effective amount of a preparation of essential oils comprising sage (*Salvia triloba*), thyme (*Thymus capitatus*) and cumin (*Cuminum cyminum*) wherein the sage, thyme and cumin are combined in the proportions 50%, 43%, and 7% weight to total volume of the preparation respectively, to a human subject in need thereof;

the administering comprising administering a dosage of 70 mg of said preparation one to four times a day; and evaluating prostaglandin levels after administering the dosage.

4. The method of claim 3, wherein the symptoms of inflammation and smooth muscle contraction in a human are one or more symptoms of menstrual cramps selected from the group consisting essentially of bloating, nausea, headache, backache, and mood swings.

5. A method of reducing uterine contractions induced by prostaglandin F2α or prostaglandin E2 in a human (*Homo sapiens*) by administering an effective amount of a preparation of essential oils comprising (*Salvia triloba*) thyme (*Thymuscapitatus*) and cumin (*Cuminum cyminum*) wherein the sage, thyme and cumin are combined in the proportions 50%, 43%, and 7% weight to total volume of the preparation respectively, to a human subject in need thereof, the administering comprising administering a dosage of 70 mg of said preparation one to four times a day.

6. The method of claim 3 wherein the dosage is administered in a soft gel capsule.

\* \* \* \* \*